United States Patent [19]
Errico

[11] Patent Number: 6,139,548
[45] Date of Patent: *Oct. 31, 2000

[54] SLIDING SHAFT VARIABLE LENGTH CROSS-LINK DEVICE FOR USE WITH DUAL ROD APPARATUS

[75] Inventor: Joseph P. Errico, Far Hills, N.J.

[73] Assignee: Spinal Concepts, Inc., Austin, Tex.

[*] Notice: This patent is subject to a terminal disclaimer.

[21] Appl. No.: 09/059,108

[22] Filed: Apr. 13, 1998

Related U.S. Application Data

[63] Continuation of application No. 08/549,977, Oct. 30, 1995, Pat. No. 5,752,955.

[51] Int. Cl.$^7$ .................................................. A61B 17/70
[52] U.S. Cl. .................................. 606/61; 606/69; 606/72
[58] Field of Search .............................. 606/60, 61, 69, 606/70, 72, 73

[56] References Cited

U.S. PATENT DOCUMENTS

| | | | |
|---|---|---|---|
| 5,005,562 | 4/1991 | Cotrel . | |
| 5,154,718 | 10/1992 | Cozad et al. | 606/61 |
| 5,275,600 | 1/1994 | Allard et al. | 606/61 |
| 5,306,307 | 4/1994 | Senter et al. . | |
| 5,306,309 | 4/1994 | Wagner et al. . | |
| 5,395,370 | 3/1995 | Muller et al. | 606/61 |
| 5,425,772 | 6/1995 | Brantigan . | |
| 5,437,669 | 8/1995 | Yuan et al. . | |
| 5,569,246 | 10/1996 | Ojima et al. . | |
| 5,609,635 | 3/1997 | Michelson . | |
| 5,667,507 | 9/1997 | Corin et al. . | |
| 5,752,955 | 5/1998 | Errico . | |
| 5,785,711 | 7/1998 | Errico et al. . | |

FOREIGN PATENT DOCUMENTS

| | | |
|---|---|---|
| 97/38640 | 10/1997 | WIPO . |
| 98/12976 | 4/1998 | WIPO . |
| 98/14142 | 4/1998 | WIPO . |

*Primary Examiner*—Michael Buiz
*Assistant Examiner*—Daphna Shai
*Attorney, Agent, or Firm*—Conley, Rose & Tayon, PC

[57] ABSTRACT

A compression locking variable length cross-link device having a pair of rod hooking elements, each having rod securing and coupling ends. The coupling ends are slidably engaging by the insertion of one into the receiving socket of the other and for selective locking to one another independent of the relative separation of the rod securing ends. Each hooking element has a curvate end formed from flat material which has been shaped into a hook conformation to cup the lateral outside surface of a corresponding rod. A set screw positioned through a hole in the top of the curved end locks the curvate end to the rod. In a first embodiment, one (a first) rod hooking element has a uniform cylindrical portion which may also include a knurled surface. The corresponding (second) element has a tubular portion including an axial receiving volume having an opening into which the cylindrical portion of the first element may be slidably inserted. The exterior surface of the tubular portion of the second element includes a slotted, threaded and tapered tip which is wider at the end thereof. A nut may be engaged on the threads of the tubular portion and advanced onto the tapered portion thereof to cause the slots to narrow, crush locking the surfaces of the inner volume and the shaft together, thereby securing the two elements at a specific separation. Set screws may then be utilized to compress and lock the rods to the curvate rod securing ends of each element.

18 Claims, 6 Drawing Sheets

SLIDING SHAFT VARIABLE LENGTH CROSS-LINK DEVICE FOR USE WITH DUAL ROD APPARATUS

This is a continuation of application Ser. No. 08/549,977 filed Oct. 30, 1995, now U.S. Pat. No. 5,752,955.

BACKGROUND OF THE INVENTION

1. Field of the Invention

This invention relates generally to a mechanical cross-link device for use with dual rod orthopedic implant apparatus. More particularly, an embodiment relates to a novel device which is fixed to each rod dual of a rod implant apparatus, and maintains and enhances the rigidity of the apparatus along a direction which is substantially transverse to the customary vertical orientation of the rods.

2. Discussion of the Prior Art

The bones and connective tissue of an adult human spinal column consist of an upper portion (the cervical, thoracic, and lumbar regions) having more than 20 discrete bones, and a lower portion which consists of the sacral bone and the coccygeal bodies. The bones of the upper portion are generally similar in shape, as will be more fully described hereinbelow with respect to FIGS. 1, 2 and 3. For the purpose of describing this invention, the sacral bone shall be distinguished from the spinal column; the spinal column, therefore, comprising for the purposes of this description, only the cervical, thoracic, and lumbar vertebrae.

Figure 1:
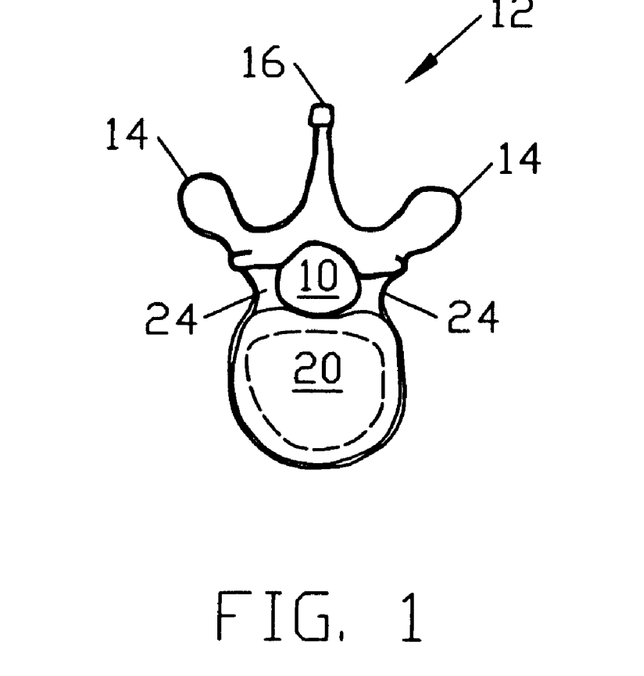
FIG. 1 is a top view of a vertebra of the human spine.
Figure 2:
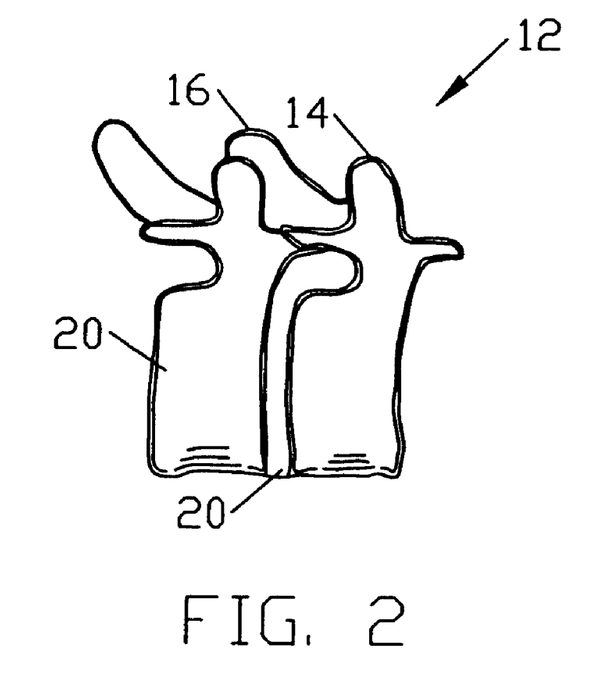
FIG. 2 is a side view of a sequence of vertebrae of the human spine.
Figure 3:
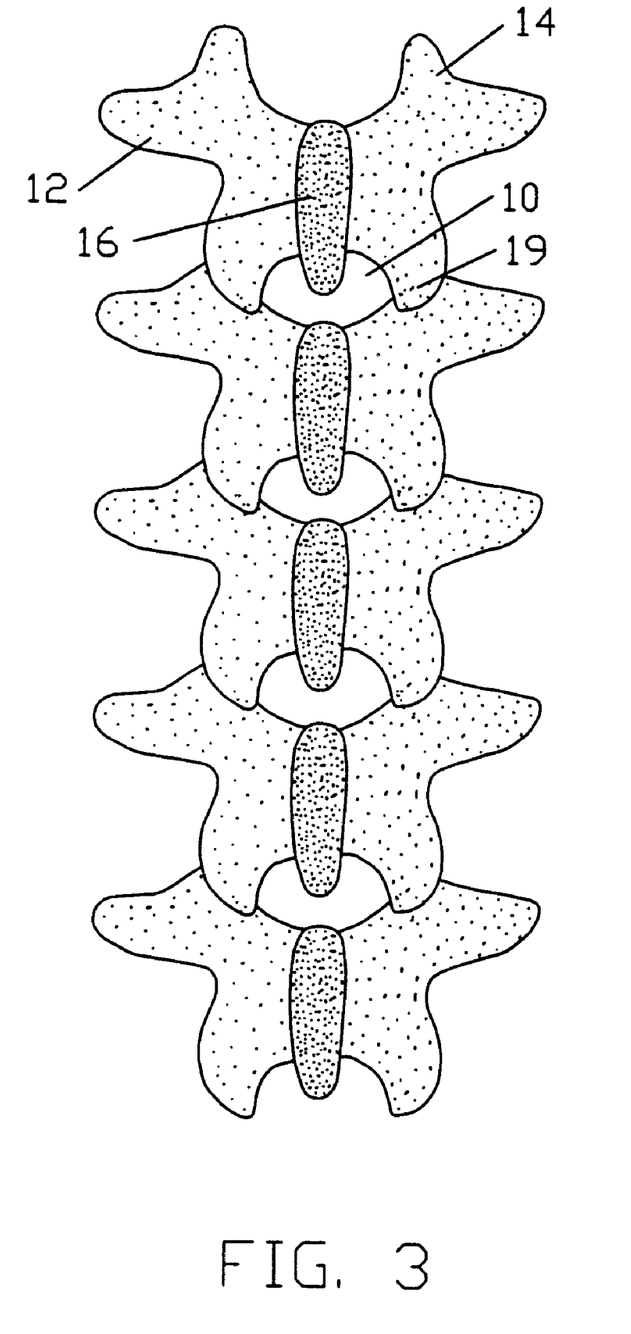
FIG. 3 is a posterior view of a sequence of vertebrae of the human spine.

The vertebrae vary in size, but are each similarly coupled to adjacent bones by a tri-joint complex. The tri-joint complex consists of an anterior disc and the two posterior facet joints, the anterior discs of adjacent bones being cushioned by cartilage spacers referred to as intervertebral discs. Referring now to FIGS. 1, 2 and 3, top, lateral, and posterior views of typical vertebral bones of the spinal column are shown. The spinal cord is housed in the central canal 10, protected from the posterior side by a shell of bone called the lamina 12. The lamina 12 has three large protrusions, two of these extend laterally from the side ends thereof and are referred to as the transverse processes 14. The third extends back and down from the center of the lamina and is called the spinous process 16. The lamina 12 defines an arched shape about the posterior of the spinal cord, the arched shape having lateral portions 13a,13b which are generally straight, and which meet beneath the spinous process at a curved surface 15.

The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14,16.

Referring specifically to FIG. 3, the stacking of vertebrae is shown from the posterior. From the posterior, each vertebra is coupled to the one above and below via facet joints 19 on either side of an opening into the spinal canal 10.

In its entirety, the spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion. Genetic or developmental irregularities, trauma, chronic stress, tumors, and disease, however, can result in spinal pathologies which either limit this range of motion, or which threaten the critical elements of the nervous system housed within the spinal column.

A variety of systems have been disclosed in the art which achieve this immobilization by implanting artificial assemblies in, or on, the spinal column. These assemblies may be classified by their position relative to the spine, as anterior, posterior, or lateral implants. Anterior and lateral assemblies generally comprise short structures which support only a few adjacent vertebral bodies. Conversely, posterior implants often comprise pairs of elongate vertically aligned rods for stabilizing both short and long segments of the spine. Such posterior rods are coupled to the back of the spinal column via hooks which slip under the lamina, means for attaching to the transverse process, and/or by screws which are inserted through the pedicle bone. In order to provide enhanced torsional rigidity, these apparatuses generally include cross-linking devices which couple the rods together transverse to the axis (vertical axis) of the apparatuses.

Figure 4:
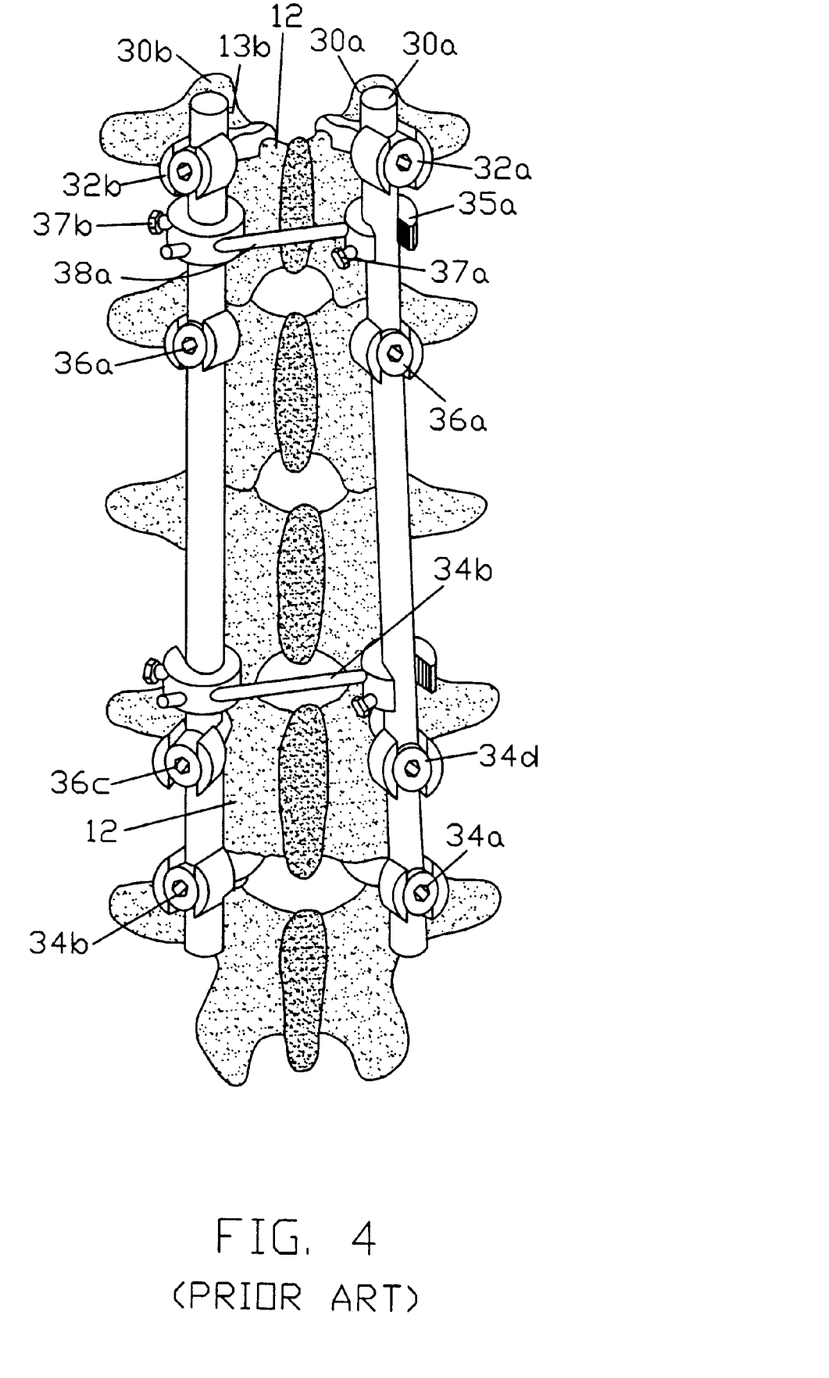
FIG. 4 is a posterior view of a dual rod apparatus of a prior art instrumentation as set forth in U.S. Pat. No. 5,005,562 to Cotrel, including cross-link devices.

Referring now to FIG. 4, U.S. Pat. No. 5,005,562 to Cotrel teaches such a dual rod apparatus which includes a pair of rods 30a,30b, which are each coupled to the spine via hooks 32a,34a and 32b,34b, respectively, as well as pedicle screws 36a,36d and 36b,36c, respectively. The rods 30a,30b are further stabilized by cross-link devices 38a,38b. These cross-link devices 38a,38b each include a pair of U-shaped gripping elements 35a,35b which may receive the rod 30a, 30b respectively. Each of the gripping elements includes a first threaded hole which extends from the outer lateral surface into the inner surface of the U-shaped rod receiving region. The gripping elements 35a,35b are fixed to the rods 30a,30b by set screws 37a,37b which are positioned in the first holes such that tightening of the set screws locks the rod 30a,30b in the gripping element. The gripping elements 35a,35b are coupled together by a threaded rod 33 which permits the gripping elements to be selectively spread or brought closer together, in accordance with the relative position of the rods 30a,30b. The threaded rod 33 extends through a second set of threaded holes in the gripping elements 35a,35b.

The bulkiness of each of the gripping elements 35a,35b, required so that it may receive the threaded rod 33, is difficult for the surgeon to use easily under operative conditions. The size of the gripping elements, and the relative position of the set screws often cause substantial difficulty with respect to the tightening of same because of their positions relative to the operative access. This bulkiness also reduces available bone graft surface area, which is critical for a successful fusion and long term immobilization. In addition, in order for a surgeon to selectively vary the spread of the gripping elements 35a,35b, one of the gripping elements must be rotated relative to the other, thus requiring the cross-link to be removed (loosening the set screws and withdrawing the device entirely from the operative site). This is particularly burdensome with respect to providing the surgeon with the ability to apply an inward force to the rods 30a,30b as the spread may not be varied in situ.

It is therefore, desirable to provide a cross-link device which provides a less bulky profile, therein providing increased area for bone grafting.

It is also desirable to provide a cross-link device which provides the surgeon with the ability to lock the device to the rods more easily than prior cross-link devices.

It is also desirable to provide a cross-link device which provides the surgeon with the ability to vary the spread of the rod gripping portions in situ, so that in doing so, the surgeon is not required to withdraw the device from the patient.

It is also desirable to provide a cross-link device which permits the surgeon to use the variable spread of the device to impart an inward force relative to the two rods, for the purposes of enhanced rotational stability.

Other features not explicitly stated will be set forth, and will be more clearly understood, in conjunction with the descriptions of the preferred embodiments disclosed hereafter.

SUMMARY OF THE INVENTION

In one embodiment a locking variable length cross-link device may be affixed to the rods of a dual rod implant apparatus. The present invention may be practiced in a variety of different embodiments; those enclosed herein being representative of preferred ones of the invention.

The embodiment described herein includes a pair of rod hooking elements formed of a substantially rigid material, for example medical grade steel or titanium. Each of the pair of rod hooking elements has a first end and a second end. The first end of each element is curvate so as to receive therein and/or seat against and hook to the lateral outside surface of a rod of a dual rod apparatus. Each of these first ends further includes a through hole for receiving a set screw. The set screw positioned therein is designed to be threadably tightened downward onto the corresponding rod seated in the first end, therein locking the rod and element together.

With respect to the second cylindrical ends, the first rod hooking element includes a simple straight shaft of uniform diameter. Preferred variations of this element, however, may also include a roughened surface on the shaft portion for the purpose of increasing the coefficient of friction of the shaft so that it may be gripped more securely. The second end of the other rod hooking element includes a shaft receiving tube having a slotted, tapered, and threaded tip. More particularly, the second end is tubular, forming a cylindrical sleeve into which the shaft of the first element may be slidably disposed. The tip of the tube has an external threading and has at least one slot extending coaxially with the tube portion, for a short distance from the opening. The threaded and slotted portion of the tip of the tube is also tapered outward, so that the tip of the tube widens toward the opening.

The coupling of these two rod hooking elements is achieved by the insertion of the shaft of the first element into the cylindrical shaft receiving tube portion of the second element, to a desired depth. Then a nut is introduced onto the threading at the tip of the tube, the subsequent tightening of which causes the slots to narrow, and the inner surface of the tube to compress against the shaft of the first element. A mutual crush lock thereof holds the two elements together at the desired spread. It is understood that the inner surface of the tubular recess may comprise a roughening so as to enhance the force of friction holding the shaft in the tube.

It is intended that prior to the tightening of the nut and the corresponding narrowing of the slots and opening of the receiving tube, the first and second elements may be spread or brought together to the extent provided by the respective lengths of the shaft and the sleeve. This permits each of the rod securing portions to be seated snugly against its corresponding rod independent of the mutual separation of the pair.

DETAILED DESCRIPTION OF THE PREFERRED EMBODIMENT

While a particular embodiment and method of implantation will be described more fully hereinafter with reference to the accompanying drawings, it is to be understood at the outset that persons skilled in the art may modify the invention herein described while achieving the functions and results of this invention. Accordingly, the descriptions which follow are to be understood as illustrative and exemplary of specific structures, aspects and features within a broad scope and not as limiting of such broad scope.

Figure 5:
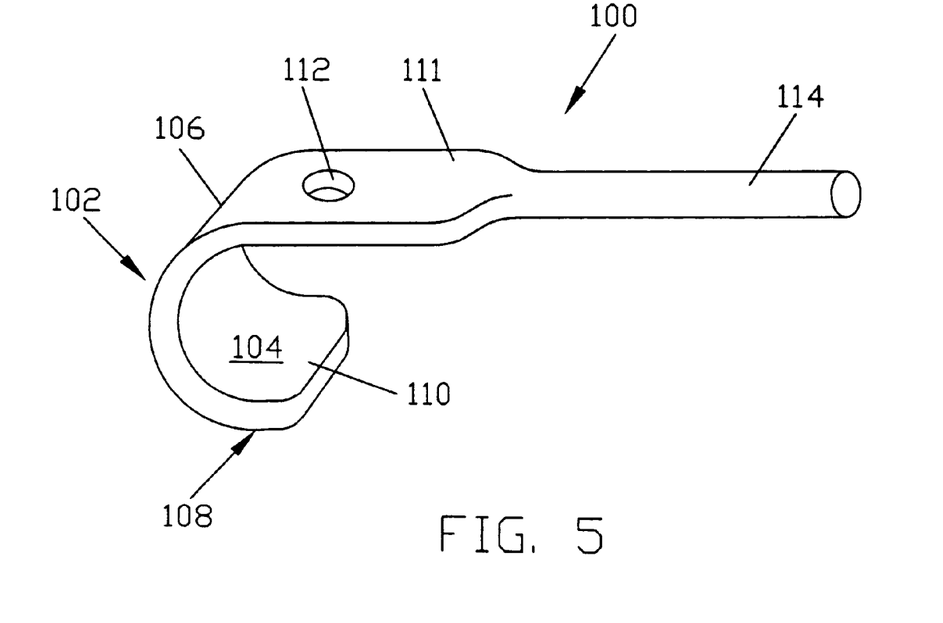
FIG. 5 is a side perspective view of a first rod hooking element.

Referring now to FIG. 5, a first rod hooking element 100 of a first embodiment is provided in a side perspective view. As with all elements, this rod hooking element may include a high strength material, for example medical grade steel or titanium compounds, which have been found ideally suited for implantation into the human body. The first rod hooking element 100 shown in FIG. 5 has a first end 102 formed of a thin and flat sheet of metal which has been curved to the shape of a hook. The hook has a semi-circular curvature defined by an inner surface 104 and an outer surface 106. The lower portion 108 of the semi-circular hook extends tangentially for a small distance, parallel to the remainder of the element. The curve is semi-circular so that it can cup and hook to the lateral outside surface of a first rod of a dual rod apparatus. The lower extending portion 108 provides an additional locking surface 110 against which the rod may be compressed by a locking means described more fully below.

The top portion 111 of the first end 102 includes a through hole 112 which is threaded and extends from a point on the top surface of the first end 102 which is adjacent to the initial curvature of the hook portion 102 to the underside of the same. Inasmuch as a set screw (set forth with respect to FIG. 6) is to be directed therethrough to lock the element 100, and more specifically the first end 102 thereof, to a rod of the implant assembly, the through hole 112 may be angled such that the insertion and subsequent tightening of the set screw drives same toward the inner surface 104 of the hook. Such a preset angle of the through hole orientation enhances the locking strength of the set screw by increasing the cupping surface against which the rod is crushed.

The other end 114 of the rod hooking element includes a shaft extending out from the first rod securing portion, said shaft having a generally uniform diameter. It is understood that the shaft 114 may have a surface roughening thereon, which increases the coefficient of static friction thereof, so that it may be held more securely by a surface on surface compression lock. This surface roughening may further include a diamond knurl.

Figure 6:
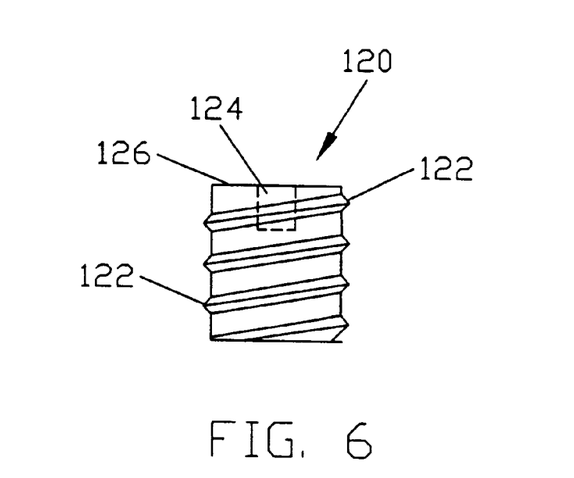
FIG. 6 is a side view of a set screw.

Referring now to FIG. 6, a side view of the set screw 120 which is used to lock the rod to the first end 102 of the rod hooking element 100 (and for applying a compression pressure as described in regards to the second embodiment set forth herein) is provided. The set screw 120 includes a surface threading 122 which is ideally suited to the threading of the through hole 112. The screw 120 further includes a recess 124 in the top 126 thereof, the recess having an internal conformation which may be engaged by a suitable tool for applying a torsional force thereto, for example a slot for a screwdriver or a hexagonally angled interior wall for an allen wrench.

Figure 7:
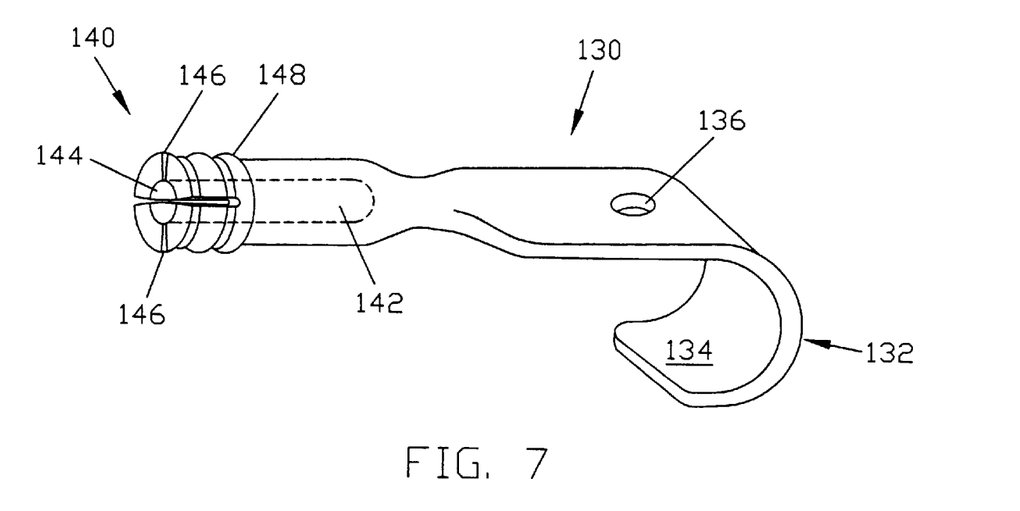
FIG. 7 is a side perspective view of a second rod hooking element.
Figure 8:
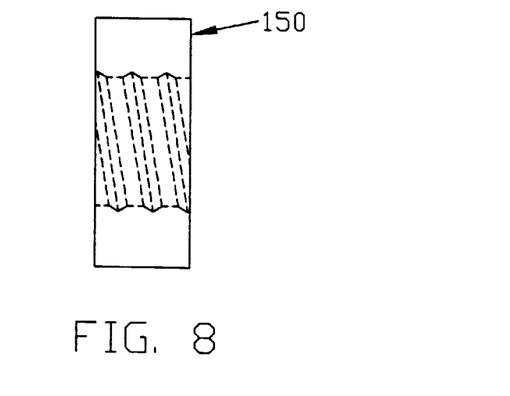
FIG. 8 is a side view of a tightening nut which threadably mates to a threading portion of the second rod hooking element illustrated in FIG. 7.

Referring now to FIGS. 7 and 8, a side perspective view of the second rod hooking element 130 and a side view of the nut 150 are provided. Specifically referring to FIG. 7, the second element 130 includes a rod securing end 132 which is substantially similar to the equivalent feature of the first element 100. More specifically, the rod securing end 132 thereof has a curvate shape and an interior surface 134 for seating against a lateral outside surface of the second rod of the dual rod apparatus. This curvate end 132 includes a through hole 136 for receiving a set screw 120 for locking the rod to the curvate shaped end.

The other end 140 of this second rod hooking element 130 is tubular, having an axial cylindrical inner volume 142. The end of the cylindrical inner volume forms an opening 144 at the tip of the second end 140, through which opening 144 the shaft 114 of the first element 100 may be slidably inserted. The inner surface of this volume 142 may include a surface roughening similar to, or at least ideally suited for engaging, the preferred roughened outer surface of the shaft 114. This surface roughening may further include a diamond knurl.

The tip portion of the tubular end 140 includes at least one slot 146 which extends axially from the opening 144. The tip is also tapered outward so that the outer surface widens toward the opening 144. The slots 146 permit the opening to contract via a radially inward application of force. Inasmuch as it is the compression of the inner surface of the tubular portion 140 (which defines the cylindrical volume 142) against the shaft 114 of the first element 100 which provides the selective locking of the two elements together, a means for applying said radially inward force is provided. The exterior surface of the tubular portion, therefore, includes a threading 148 at the tip thereof so that a nut may be introduced thereonto.

FIG. 8 is a side view of the nut 150 which is threaded onto the threads 148 of the tubular portion 140. Advancement of the nut 150 onto the tapered portion provides the radially inward force to close the at least one slot 146 and lock the shaft 114 in the inner volume 142. The tightening nut 150 is understood to be positioned about the tubular portion 140 prior to the introduction of the shaft 114 therein, and preferably, the second element is provided to the surgeon with the nut 150 already about the second element 130, having been introduced thereon either by an operating room nurse, or having been assembled by the manufacturer.

Figure 9:
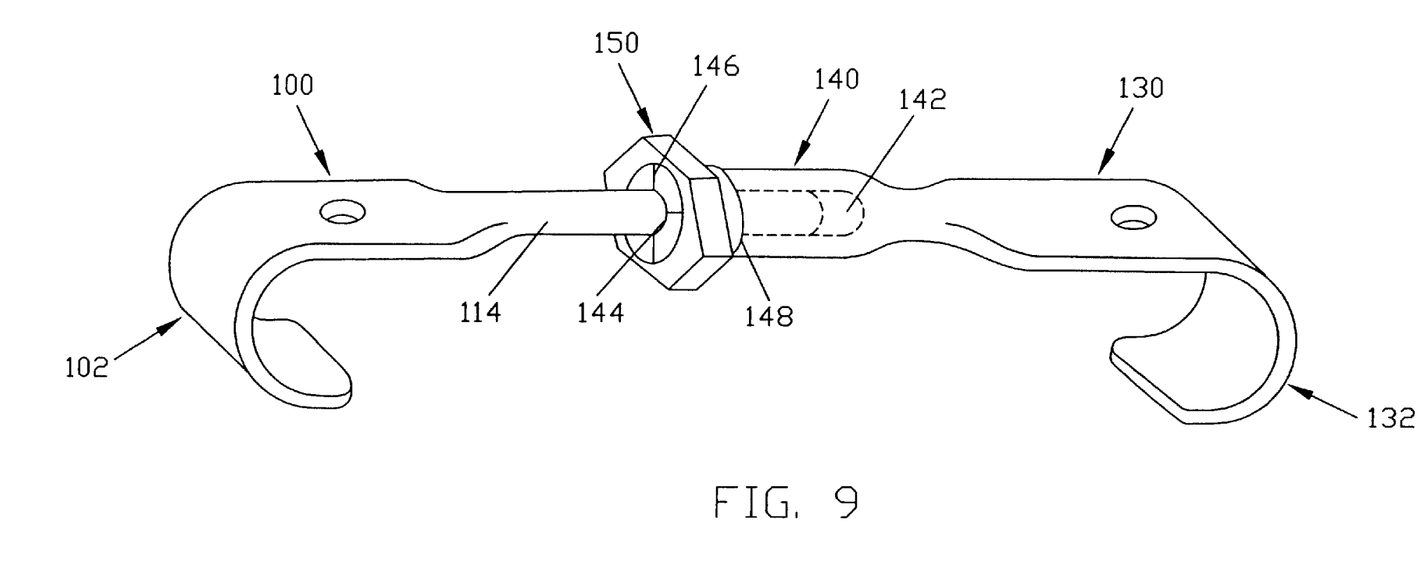
FIG. 9 is a side perspective view of a fully assembled embodiment including the elements illustrated in FIGS. 5,7, and 8.

With reference now to FIG. 9, in which a fully assembled first embodiment is provided in a side perspective view, the method of assembly and the locking of the elements is described. First the proper site for the fixation of the dual rod cross-link device is identified by the surgeon. The site should provide enough space along the rods for engagement of rod securing ends 102 and 132. Once this site is found, and the space separating the rods is cleared of all obstacles (for example, the spinous process), the shaft 114 of the first element 100 is inserted through the opening 144 of the second end 140 of the second element 130 and into the inner volume 142 thereof to a desired depth. At this point the shaft 114 remains slidable relative to the second element 130 so that the pair may be selectively spread or drawn together by an amount determined solely by the mutual engagement of the shaft and the inner volume. The tightening nut 150 is then rotationally engaged onto the threading 148 of the tapered and slotted tip so as to cause the opening to contract via the narrowing of the at least one slot 146. This locks the shaft 114 to the surface defining the inner volume at the desired depth.

Once the length of the cross-link has been set, the set screws 120 may be tightened down, thereby locking the element 100 and 130 to the rods themselves.

While there has been described and illustrated a cross-link device for coupling dual rods of orthopedic apparatus together and providing enhanced stability thereto, it will be apparent to those skilled in the art that variations and modifications are possible without deviating from the broad spirit and principle of the present invention which shall be limited solely by the scope of the claims appended hereto.

I claim:

1. An orthopedic rod connecting assembly, comprising:
   a first element comprising a first end and a second end, wherein the first end of the first element is configured to receive a spinal rod during use and wherein the second end of the first element comprises a shaft;
   a second element comprising a first end and a second end, wherein the first end of the second element is configured to receive a spinal rod during use, and wherein the second end of the second element defines a sleeve configured to receive the shaft of the first element during use;
   wherein the sleeve is compressible, effective to be pressed against the shaft of the first element, when the shaft is disposed in the sleeve during use, and wherein one or more of the inner surface of the sleeve and the outer surface of the shaft are textured, effective to increase the friction between the inner surface of the sleeve and a shaft disposed in the sleeve during use.

2. The assembly of claim 1, wherein the sleeve and the shaft form a crush lock during use.

3. The assembly of claim 1, wherein the sleeve comprises one or more slots for facilitating compression of the sleeve during use.

4. The assembly of claim 1, wherein an outer surface of the second end of the second element comprises tapered threading, and the assembly further comprises a nut configured to be threadably advanced onto the tapered threading and to compress the sleeve during use.

5. The assembly of claim 1, wherein at least one of the first end of the first element and the first end of the second element comprise a hook shaped member for receiving a rod and a locking device to secure a rod to the member.

6. The assembly of claim 5, wherein at least one locking device comprises a set screw.

7. The assembly of claim 6, wherein at least one set screw is configured to urge a rod held in the hook shaped member against the inner surface of the hook during use.

8. A method of manufacturing an orthopedic rod connecting assembly, comprising:
   providing a first element comprising a first end and a second end, wherein the first end of the first element is configured to receive a first rod during use, and wherein the second end of the first element comprises a shaft; and providing a second element comprising a first end and a second end, wherein the first end of the second element is configured to receive a second rod during use, and wherein the second end of the second element defines a compressible sleeve for receiving the shaft of the first element during use;

wherein the second end of the second element further comprises one or more slots and tapered threading; and wherein the method further comprises providing a nut for securing the first element to the second element, such that the nut is threadable on the tapered threading effective to crush lock the second end of the first element to the second end of the second element during use.

9. The method of claim 8, wherein at least one of the first end of the first element and the first end of the second element comprise a hook shaped member for receiving a rod and a locking device to secure a rod to the member.

10. The method of claim 9, wherein at least one locking device comprises a set screw.

11. A method of increasing the rigidity of an orthopedic rod implant system in a direction substantially transverse to the length of an implanted rod, comprising:

providing a first element comprising a substantially hook shaped end for securing a rod, and a shaft connected thereto;

providing a second element comprising a substantially hook shaped end for securing a rod, and a sleeve connector connected thereto, wherein the sleeve connector is configured to receive the shaft, and further wherein the diameter of the sleeve is compressible during use;

securing a rod to the hook shaped end of the first element and securing a second rod to the hook shaped end of the second element;

inserting the shaft into the sleeve and positioning the shaft in the sleeve to achieve a desired distance between the first rod and the second rod; and compressing the sleeve effective to press the sleeve against the shaft;

wherein the sleeve comprises one or more slots, and wherein the sleeve comprises external threading configured to reduce the diameter of the sleeve when a nut is advanced onto the threading and the method further comprises providing a nut threadable on the external threads and tightening the nut in order to lock the shaft in the sleeve.

12. The method of claim 11, wherein at least one rod is secured to a hook shaped end by a set screw.

13. The method of claim 11, wherein the first rod and the second rod are disposed in substantially parallel orientation.

14. A method of increasing the rigidity of an orthopedic rod implant system in a direction substantially transverse to the length of an implanted rod, comprising:

providing a first element comprising a substantially hook shaped end for securing a rod, and a shaft connected thereto;

providing a second element comprising a substantially hook shaped end for securing a rod, and a sleeve connector connected thereto, wherein the sleeve connector is configured to receive the shaft, and further wherein the diameter of the sleeve is compressible during use;

securing a rod to the hook shaped end of the first element and securing a second rod to the hook shaped end of the second element;

inserting the shaft into the sleeve and positioning the shaft in the sleeve to achieve a desired distance between the first rod and the second rod; and compressing the sleeve effective to press the sleeve against the shaft;

wherein one or more of the inner surface of the sleeve and the outer surface of the shaft are textured, effective to increase the friction between the inner surface of the sleeve and a shaft disposed in the sleeve during use.

15. The method of claim 14, wherein the sleeve comprises one or more slots.

16. The method of claim 15, wherein the sleeve comprises external threading configured to reduce the diameter of the sleeve when a nut is advanced onto the threading and the method further comprises providing a nut threadable on the external threads and tightening the nut in order to lock the shaft in the sleeve.

17. The method of claim 14, wherein at least one rod is secured to a hook shaped end by a set screw.

18. The method of claim 14, wherein the first rod and the second rod are disposed in substantially parallel orientation.

* * * * *